United States Patent [19]

Telschow et al.

[11] Patent Number: 5,237,085

[45] Date of Patent: Aug. 17, 1993

[54] PROCESS FOR THE FORMATION OF PENTAERYTHRITOL-BASED PHOSPHOROUS HETEROCYCLES

[75] Inventors: Jeffrey E. Telschow, Tarrytown; Edward D. Weil, Hastings-on-Hudson, both of N.Y.

[73] Assignee: Akzo N V, Arnhem, Netherlands

[21] Appl. No.: 911,868

[22] Filed: Jul. 10, 1992

[51] Int. Cl.$^5$ .............................................. C07F 9/02
[52] U.S. Cl. ...................................... 558/74; 558/73; 568/12
[58] Field of Search ....................... 568/12; 558/74, 73

[56] References Cited

U.S. PATENT DOCUMENTS 4,454,064  6/1984  Halpern et al. ..................... 558/74

*Primary Examiner*—Marianne M. Cintins
*Assistant Examiner*—Margaret J. Page
*Attorney, Agent, or Firm*—Richard P. Fennelly; Louis A. Morris

[57] ABSTRACT

A process for the formation of pentaerythritol-based phosphorus heterocycles comprises the reaction of a pentaerythritol polyol, e.g., pentaerythritol, with a trivalent or pentavalent phosphorus compounds, e.g., a phosphorus oxytrihalide, a triorganophosphite, or a phosphorus trihalide, in an aryl phosphate solvent at elevated temperature.

8 Claims, No Drawings

PROCESS FOR THE FORMATION OF PENTAERYTHRITOL-BASED PHOSPHOROUS HETEROCYCLES

BACKGROUND OF THE INVENTION

It is known to react pentaerythritol polyols with either a trivalent or pentavalent phosphorus compound in order to form a heterocyclic compound containing phosphorus which is derived from the foregoing class of reagents One compound of this type is pentaerythritol phosphate which can be formed by the reaction of pentaerythritol and phosphorus oxychloride in solvent. U.S. Pat. No. 4,454,064 indicates that a variety of solvents have been used in the past in such a reaction. For example, petroleum ether and benzene are identified as solvents which had been used before the invention described in U.S. Pat. No. 4,454,064. Representative solvents which are described in this patent include dioxane, the preferred solvent, ethylene glycol dimethyl ether, diethylene glycol dimethyl ether, chlorobenzene, toluene, xylene, acetonitrile, sulfolane, and tetrachloroethylene. The solvents are indicated as being ones which should have a boiling point of at least 75° C., preferably in the range of 75° C. to about 125° C.

BRIEF DESCRIPTION OF THE PRESENT INVENTION

The present invention relates to a novel process for the formation of pentaerythritol-based phosphorus heterocycles which comprises the reaction of a pentaerythritol polyol with either a trivalent or pentavalent phosphorus compound using an aryl phosphate solvent at elevated temperature.

DETAILED DESCRIPTION OF THE PRESENT INVENTION

The present invention is directed to a process for the formation of pentaerythritol-based phosphorus heterocycles which uses as one essential reagent a pentaerythritol polyol which can be selected from pentaerythritol itself, dipentaerythritol, tripentaerythritol, or mixtures of any of these three types of polyols. The terminology "pentaerythritol-based" as used herein is meant to encompass compounds containing the structural unit —$C(CH_2OH)_3$ which is contained in either pentaerythritol or its dimeric or trimeric derivatives, dipentaerythritol and tripentaerythritol.

The particular type of trivalent or pentavalent phosphorus compound which is to be selected for use in the present invention would depend upon the type of phosphorus-containing heterocycle desired. Generally speaking, the phosphorus compound can be selected from trivalent or pentavalent phosphorus compounds with representative trivalent phosphorus compounds being phosphorus trihalides or organophosphites (e.g., triphenyl phosphite). Representative pentavalent phosphorus reagents for use in the present process include the phosphorus oxytrihalides such as phosphorus oxytrichloride.

In the case of pentaerythritol as a reagent, the reaction of the pentavalent phosphorus oxytrihalide in equimolar amount will yield the aforementioned type of pentaerythritol phosphate. Reaction of an equimolar amount of either the organophosphite or the phosphorus trihalide will yield the analogous pentaerythritol phosphite such as shown in Example 2, below. The use of two moles of a phosphorus trihalide will result in the formation of a spirobischlorophosphite, as more fully shown in Example 3 below. In like manner, two moles of phosphorus oxychloride can be reacted with one mole of dipentaerythritol with evolution of six moles of hydrogen chloride and formation of dipentaerythritol diphosphate.

The novel solvent employed in the present invention is, preferably, a neutral ester of a phosphorus acid in the +5 oxidation state which is stable (free of acid generation) at the selected reaction temperature. It is, for example, an aryl phosphate solvent which has a relatively high boiling point, e.g., from about 400° C. to about 500° C., such as triphenyl phosphate, cresyl diphenyl phosphate, tricresyl phosphate, isopropylphenyl diphenyl phosphate, t-butylphenyl diphenyl phosphate, and tetraphenyl resorcinol diphosphate. The use of this novel type of solvent in the present invention has certain advantages over the prior art solvents that are known to persons of ordinary skill in the art. For one thing, the solvent used in the present invention is a flame retardant in its own right and, to the extent that it is present as a contaminant in the flame retardant product, it is unlikely to be a problem when the product is used. Secondly, the phosphate solvent is moderately polar to promote the solubility of the reacting species. Thirdly, the very high boiling points and good thermal stability of the phosphates allow for distillation of rather high boiling reaction by-products, such as phenol, without contamination from the solvent. Fourthly, the general water insolubility of the phosphate solvents used in the present invention allows for aqueous wash, if necessary, for purification of the solvent by dissolving water-soluble species (including acid or base-soluble species). Thus, the recyclability of the phosphate solvent is enhanced.

The present invention is further understood by reference to the Examples which follow.

EXAMPLE 1

In a 250 mL four-necked reaction flask fitted with a mechanical stirrer, pot thermometer, addition funnel, and condenser with gas outlet were placed 42.5 g (0.313 mole) of pentaerythritol and 150 mL of PHOSFLEX 41P brand of isopropylated triphenyl phosphate under nitrogen. The mixture was stirred and heated at 95° C. as 49.2 g (0.321 mole) of phosphorus oxychloride was added dropwise over five hours. The resulting white slurry was heated to 100° C. with a nitrogen gas sparge for eight hours to remove HCl. The mixture was cooled to 50° C. and filtered. The solid was washed three times with 40 mL of hexane and dried at 100° C./2 mm Hg for sixteen hours to give 42.3 g (71.2% yield) of crude pentaerythritol phosphate alcohol (2,6,7-trioxa- 1-phosphabicyclo [2.2.2]octane-4-methanol-1-oxide). The product had a $^{31}P$ NMR resonance at —6.0 ppm in $d_6$-DMSO.

EXAMPLE 2

In a 500 mL four-necked flask equipped with a mechanical stirrer, pot thermometer, and 3.5 inch Vigreux column plus distilling head, were placed 68.1 g (0.50 mole) of pentaerythritol, 155.2 g (0.50 mole) of triphenyl phosphite, 115 mg (5 mmoles) of sodium metal, 471 mg (5 mmoles) of phenol, and 100 mL of the PHOSFLEX 41P brand material. The mixture was heated with stirring at 145°–155° C. under 70 mm Hg pressure as 141.3 g (100% yield) of by-product phenol was distilled as formed over seven hours. The resulting, nearly colorless solution contained the pentaerythritol phosphite alcohol, 2,6,7-trioxa-1-phosphabicyclo[2.2.2]octane-4-methanol in about 92% purity, by $^{31}$P NMR (95.2 ppm in d$_6$-DMSO).

EXAMPLE 3

In a 250 mL four-necked flask fitted as in Example 1 were placed 40.8 g (0.30 mole) of pentaerythritol, 60 mg (0.63 mmole) of anhydrous magnesium dichloride, and 50 mL of the PHOSFLEX 41P brand material under nitrogen. The mixture was stirred and heated to 45°-50° C. during the one and one-half hour dropwise addition of 65.3 mL (103 g, 0.75 mole) of phosphorus trichloride. The temperature was increased to 95° C. over the next hour and held there for five hours during a nitrogen sparge to remove HCl. The solution, which crystallized on cooling, showed mainly one product peak at 149 ppm by $^{31}$P NMR in d$_6$-DMSO, consistent with 3,9-dichloro-2,4,8,10-tetraoxa-3,9-diphosphaspiro[5.5]undecane.

The foregoing Examples are set forth to illustrate certain preferred embodiments of the present invention but should not be construed in a limiting sense. The scope of protection which is sought is set forth in the claims which follow.

We claim:

1. A process for the formation of pentaerythritol-based phosphorus heterocycles which comprises the reaction of a pentaerythritol polyol with a trivalent or pentavalent phosphorus compound in an aryl phosphate solvent at elevated temperature.

2. A process as claimed in claim 1 wherein the pentaerythritol polyol is pentaerythritol.

3. A process as claimed in claim 1 wherein the trivalent phosphorus compound is selected from the group consisting of a phosphorus trihalide and an organophosphite.

4. A process as claimed in claim 1 wherein the pentavalent phosphorus compound is a phosphorus oxytrihalide.

5. A process as claimed in claim 1 wherein the pentaerythritol polyol is pentaerythritol and a trivalent phosphorus compound is used.

6. A process as claimed in claim 1 wherein the pentaerythritol polyol is pentaerythritol and a pentavalent phosphorus compound is used.

7. A process as claimed in claim 5 wherein the trivalent phosphorus compound is selected from the group consisting of a phosphorus trihalide and an organophosphite.

8. A process as claimed in claim 6 wherein the pentavalent phosphorus compound is a phosphorus oxytrihalide.

* * * * *